(12) United States Patent
Rapisarda

(10) Patent No.: US 7,368,481 B1
(45) Date of Patent: May 6, 2008

(54) PET ANTI-AGING WELLNESS SUPPLEMENT FOR CATS

(75) Inventor: Carol Osborne Rapisarda, Chagrin Falls, OH (US)

(73) Assignee: Rapisarda Family Irrevocable Trust, Chagrin Falls, OH (US)

( * ) Notice: Subject to any disclaimer, the term of this patent is extended or adjusted under 35 U.S.C. 154(b) by 482 days.

(21) Appl. No.: 11/173,203

(22) Filed: Jul. 1, 2005

Related U.S. Application Data

(63) Continuation-in-part of application No. 10/770,953, filed on Feb. 3, 2004, now Pat. No. 6,974,841, which is a continuation of application No. 10/259,147, filed on Sep. 27, 2002, now abandoned.

(51) Int. Cl.
*A61K 47/00* (2006.01)

(52) U.S. Cl. .................. 514/783; 514/276; 424/442

(58) Field of Classification Search ................ 514/251, 514/276, 783; 424/442; 426/2
See application file for complete search history.

(56) References Cited

U.S. PATENT DOCUMENTS

| | | | |
|---|---|---|---|
| 2,959,520 A | | 11/1960 | Kawajiri |
| 4,976,960 A | * | 12/1990 | Grossman et al. .......... 424/750 |
| 5,466,452 A | | 11/1995 | Whittle |
| 6,147,054 A | | 11/2000 | De Paoli Ambrosi |
| 6,214,371 B1 | | 4/2001 | Kobayashi et al. |
| 6,413,545 B1 | | 7/2002 | Alviar et al. |
| 2003/0077254 A1 | * | 4/2003 | Ramaekers ................ 424/93.3 |

* cited by examiner

*Primary Examiner*—Rob Swiatek
(74) *Attorney, Agent, or Firm*—Pearne & Gordon LLP

(57) ABSTRACT

A health and nutrition supplement dosage for pets, particularly feline pets, consisting essentially of anti-oxidant vitamins, B complex vitamins, bioflavonoids, chelated minerals, digestive enzymes, herbs, nutrients, and essential fatty acids and amino acids.

4 Claims, No Drawings

PET ANTI-AGING WELLNESS SUPPLEMENT FOR CATS

This application is a Continuation-In-Part Of U.S. application Ser. No. 10/770,953 filed Feb. 3, 2004 now U.S. Pat. No. 6,974,841, which is in turn a Continuation of U.S. application Ser. No. 10/259,147, filed Sep. 27, 2002 now abandoned.

This invention relates to a pet anti-aging wellness system providing in a natural treat formula for cats and an AM/PM dosage system for the formulation given according to body weight.

BACKGROUND OF THE INVENTION

People and pets are now living longer than ever before. Cat owners naturally want their cats to live the longest, healthiest life possible. Cats, like people, have specific nutritional needs. As the cat gets older, the aging process takes it toll. The cat tends to slow down mentally and physically.

Although the aging process is different for every animal it generally begins at maturity, somewhere between ten and twelve months of age. Cats are considered seniors at age seven and geriatrics at age 12. Shorter lived breeds like Persians become seniors at age 6.

To determine whether or not a cat is old, it's important to distinguish between chronological and biological age. Chronological age is merely the number of years a cat has lived while biological age is determined by how the cat looks, acts and feels. From an anti-aging standpoint the cats biological age is more important that its chronological age. Longevity is attributed 70% to lifestyle and 30% to genetics. Up to 90% of diseases in cats are due to the degenerative process associated with aging.

Balanced diets are essential, but alone they cannot provide a cat with optimal levels of nutrients his or her body needs. In fact, just to obtain adequate levels of vitamin E the cat would have to consume 2500 calories a day. Consuming this many calories is detrimental to the cats health and could quickly lead to obesity and several other health-related problems. Also, taking vitamins once a day may not be sufficient to provide anti-aging benefits for the cat. Many vitamins are water-soluble and are diluted and secreted from the body fairly quickly.

BRIEF DESCRIPTION OF THE INVENTION

This invention provides an anti-aging, longevity and wellness supplement that is a unique combination of natural ingredients as a flavored powder within an AM and a PM capsule that will help promote a longer, healthier life for a cat.

The supplement contains rich amounts of antioxidants including vitamins A, C, and E along with the minerals selenium and zinc. A once a day dosage may not be sufficient to provide anti-aging benefits because of the water solubility of the vitamins. An optimal dosage should be given in the morning and again before bedtime. The morning AM formulation further includes green tea, ginseng, glucosamine MSM (methyl-sulfonyl-methane) and essential fatty acids, all of which improves the cats mood, mobility and energy levels. The evening PM formula contains anti-oxidants, b-complex vitamins, digestive enzymes, colostrum and melatonin which prepares the cat for sleep and energizes its body cells.

An effective morning AM formulation for an 8-12 pound adult or senior cat is one capsule which, together, include the following ingredients in the amounts specified:

| Anti-Oxidant Vitamins | |
|---|---|
| Vitamin A (Palmitate, Alpha Carotene, Lycopene and other Carotenoids) | 113 IU |
| Vitamin C (Ascorbic Acid) | 17 mg |
| Vitamin E (d-Alpha Tocopherols) | 5.0 IU |
| Lutein | 1.0 mcg |
| Coenzyme Q10 | 1.0 mg |
| B Complex Vitamins | |
| Vitamin B-1 (Thiamine Hydrochloride) | 1.3 mg |
| Vitamin B-2 (Riboflavin Powder) | 0.55 mg |
| Vitamin B-3 (Niacin) | 1.0 mg |
| Vitamin B-3 (Niacinamide) | 12.5 mg |
| Vitamin Biotin | 8.3 mcg |
| Vitamin Folic Acid | 8.3 mcg |
| Vitamin B-12 (Cyanocobalamin) | 8.3 mcg |
| Vitamin B-5 (Calcium Pantothenate) | 2.5 mg |
| Vitamin B-6 (Pyridoxine HCL) | 0.415 mg |
| Inositol | 31.3 mg |
| Bioflavonoids | |
| Lemon Bioflavonoids | 3.125 mg |
| Chelated Minerals | |
| Zinc Gluconate | 1.0 mg |
| Selenium Chelate | 4.4 mcg |
| Chromium Chelate | 12.5 mcg |
| Vanadyl Sulfate | 8.3 mcg |
| Calcium Citrate | 1.0 mg |
| Magnesium Oxide | 1.875 mg |
| Manganese Malate | 0.65 mg |
| Digestive Enzymes | |
| Digestive Enzyme Complex (full range) consisting of: | 1.25 mg |
| Protease | 7.5 Units |
| Amylase | 30 Units |
| Lipase | 1.25 Units |
| Cellulase | 0.25 Units |
| Lactase | 5.0 Units |
| Herbs | |
| Green Tea Extract (30% polyphenols) | 17.5 mg |
| Siberian Ginseng (root) | 12.5 mg |
| Nutrients | |
| Glucosamine Hydrochloride | 100 mg |
| MSM | 31.25 mg |
| Alpha Lipoic Acid | 1.0 mg |
| L-Lysine | 12.5 mg |
| L-Taurine | 12.5 mg |
| L-Carnitine | 1.25 mg |
| Essential Fatty Acids | |
| Gamma Linolenic Acid (Borage Seed Oil) | 5.0 mg |

An effective evening PM formulation for an 8-12 pound cat is one capsule which, together, include the following ingredients in the amounts specified:

| Anti-Oxidant Vitamins | |
|---|---|
| Vitamin A (Palmitate, Alpha Carotene, Lycopene and other Carotenoids) | 113 IU |
| Vitamin C (Ascorbic Acid) | 17 mg |
| Vitamin E (D-Alpha Tocopheryl acetate) | 5.0 IU |
| B Complex Vitamins | |
| Vitamin B-1 (Thiamine Hydrochloride) | 1.3 mg |
| Vitamin B-2 (Riboflavin Powder) | 0.55 mg |

-continued

| | |
|---|---|
| Vitamin B-3 (Niacin) | 1.0 mg |
| Vitamin B-3 (Niacinamide) | 5.0 mg |
| Vitamin Biotin | 8.3 mcg |
| Vitamin Folic Acid | 8.3 mcg |
| Vitamin B-12 (Cyanocobalamin) | 8.3 mcg |
| Vitamin B-5 (Calcium Pantothenate) | 2.5 mg |
| Vitamin B-6 (Pyridoxine HCL) | 0.415 mg |
| Choline Bitartrate | 1.25 mg |
| Inositol | 31.3 mg |
| Bioflavonoids | |
| Lemon Bioflavonoids | 3.125 mg |
| Chelated Minerals | |
| Zinc Gluconate | 1.0 mg |
| Selenium Chelate | 4.4 mcg |
| Chromium Chelate | 12.5 mcg |
| Vanadyl Sulfate | 8.3 mcg |
| Calcium Citrate | 1.0 mg |
| Magnesium Oxide | 1.875 mg |
| Manganese Malate | 0.65 mg |
| Digestive Enzymes | |
| Digestive Enzyme Complex (Digezyme ™) | 1.25 mg |
| Nutrients | |
| Colostrum | 0.65 mg |
| Whey Peptides (Hydrolyzed Whey Protein) | 7.0 mg |
| Melatonin | 0.095 mg |
| Amino Acids | |
| L-Glutamine | 31.25 mg |
| L-Carnitine | 1.0 mg |
| L-Lysine | 12.5 mg |
| L-Taurine | 12.5 mg |

The following ingredients in the formulation contribute the stated benefits:

Antioxidants including Vitamins A, C and E, along with the Minerals Selenium and Zinc and the nutrients Alpha Lipoic Acid and Lutein and Coenzyme Q 10.

A pet's body naturally contains many antioxidants that work together, in a variety of ways to help protect and insure health. Antioxidants neutralize harmful compounds called free radicals. Free radicals are formed each time a cat takes a breath. Exposure to the suns ultraviolet rays, environmental toxins, pollution, heavy metals, stress, diet and drugs, including antibiotics, also contribute to their production. Billions of free radicals are formed in a cat's body each day. They cause Oxidative Stress, which damages the pet's body; in much the same way that oxygen causes iron to rust. Free radicals damage the cat's cells and can also adversely effect vital tissues, organs and even DNA, the cats genetic material. These harmful changes accumulate and have been proven to decrease the quality and length of life. Antioxidant supplementation can increase the pets healthy life span and slow the aging process by providing the body with additional defenses against free radicals and decreasing the resultant levels of oxidative damage. Oxidative damage has been associated with many of the leading age related degenerative diseases including cancer, heart disease, liver and kidney disorders as well as arthritis, diabetes, senility and cognitive dysfunction.

Vitamin A

Vitamin A is an essential nutrient that acts as an antioxidant. It is also necessary for good vision, proper bone development and healthy skin.

Vitamin C

Vitamin C is needed to regenerate and revitalize Vitamin E. It is also essential to normal collagen formation. Collagen is an integral part of the walls of the blood vessels and is part of the matrix of cartilage, tendons, ligaments, bones and skin.

Vitamin E

Vitamin E is needed to regenerate and revitalize Vitamin C. It is also important to help maintain the integrity of cell membranes, which is essential for them to function normally.

Selenium

Selenium is an essential mineral, which is incorporated into many vital enzymes in the body. Selenium also works with Vitamin E as an antioxidant to help protect against free radical oxidative damage.

Zinc

Zinc is an essential mineral and is a vital component of several biochemical and enzymatic reactions in the cat's body. In addition, zinc is needed to maintain the health and integrity of the skin and hair coat.

Lutein

Lutein is plant pigment, derived from marigolds, that functions as an Antioxidant. It has been shown to play an important role in maintaining vision, health of the eyes as well as its role in maintaining a normally functioning Immune System.

Colostrum

Colostrum is the first milk the cat receives from his (or her) mother. It provides newborn kittens with substances called antibodies, which are needed for protection from disease during the first few months of life. Colostrum is important to help maintain the health and normal functioning of the immune system, which is the body's natural defense against disease and infection.

Glucosamine

Glucosamine is an amino sugar made of molecules called Glucosaminoglycans or "GAGS". GAGS are found in almost every tissue of the body including joints, tendons, ligaments, cartilage, skin, blood vessels and urinary bladder. Glucosamine is needed to maintain normal joint fluid. Joint fluid surrounds the joints providing them with important nutrients. It helps to lubricate and cushion the joints, acting like a shock absorber during movement and insulating the bones from friction. Glucosamine is necessary to maintain the overall health and integrity of cartilage, bones, joints and the urinary bladder. It may also enhance the cat's mobility and flexibility.

MSM (methyl-sulfonyl-methane)

A unique organic form of sulfur that has an important role in the maintenance of normal joints and acts together with Glucosamine to restore normal joint function and integrity.

Manganese

A trace mineral needed for vital enzyme reactions and proper bone development. It plays a key role in supporting the bodies production of vital elements required to rebuild cartilage in damaged joints.

Chromium Picolinate & Vanadyl Sulfate

These nutrients improve blood sugar metabolism, blood lipid concentrations and reduce body fat. Together they act to increase the body's sensitivity to the hormone insulin which may reduce the risk of diabetes.

Green Tea

The Anti-oxidants in Green Tea may decrease the risk of heart disease and protect the blood vessels that nourish the heart and brain. The Epigallocatechin Gallate (EGCG) in green tea may also be cancer protective.

B-Complex Vitamins

These are critical cofactors necessary for energy production. They are essential to metabolize proteins, carbohydrates and fats. B-Complex Vitamins aid in the release of energy from foods and may help to reduce cholesterol and triglycerides in the blood.

Siberian Ginseng

The root of this plant was used for centuries in Asia as a strengthening tonic that rejuvenates and revitalizes the body. It also maintains blood glucose levels, has a role in regulation of blood pressure, strengthens the cardiovascular system and boosts immunity.

L-Glutamine

L-Glutamine is the most abundant amino acid in the body. It is the major energy source for the cells that line the small intestine of the cat's digestive track. It helps to energize the body by aiding in the maintenance of normal digestive system function. L-Glutamine is a precursor to Glucosamine, which the body uses to produce Glucosaminolglycans, (GAGS), as well as purine nucleotides, which are constituents of the cats genetic material, (DNA & RNA).

Digestive Enzymes

Digestive enzymes are important to maintain overall health. The body's production of enzymes naturally decreases with increasing age. Proper supplementation of enzymes can enhance the cat's ability to digest, absorb and utilize nutrients in his diet, which are essential for energy production and ultimately, for life itself.

Essential Fatty Acids: Linolenic Acid

Linolenic Acid is an essential fatty acid, which helps to maintain the health and normal function of the skin and hair coat. It is also necessary for the normal structure, function and integrity of the cat's heart and brain.

Senior pets on the formula may enjoy good health, boundless energy and re-attain the physical and mental attributes they enjoyed in their younger years. Most senior pets on the formula seem happier, enjoy a better mental outlook on life and once again become active members of the world in which they live.

Adult pets on the AM/PM formula may look forward to achieving optimal health, well being, quality and length of life. Cats started on the formula at the onset of adulthood may enjoy an active healthy life to the fullest.

Coenzyme Q 10

Also known as COQ10 or ubiquonone (50) belongs to a family of substances called ubiquinones. They are lipophilic, water insoluble substances involved in electron transport and energy production in the mitochondria.

Coenzyme Q 10 has anti-oxidant activity and may have cardio protective, cytoprotective and neuroprotective properties. It protects against the peroxidation of lipid membranes and inhibits the oxidation of low density lipoprotein cholesterol. There is fairly convincing evidence on its benefits in treating congestive heart failure. It may boost energy and may speed recovery of exercise related muscle exhaustion and damage. It may improve glycemic control in type 11 diabetics and evidence also indicates its potential usefulness in treating age related neurodegenerative diseases.

Alpha Lipoic Acid

Is a disulfide compound that is a cofactor in vital energy producing reactions in the body. It is also a potent biological antioxidant. It participates in the recycling of other important biological antioxidants, such as vitamin E and C, coenzyme Q 10 and glutathione. It may slow aging of the brain and may be an anti-aging substance in general. Evidence indicates it may reverse age related loss of cognitive decline and improve memory.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A health and nutrition supplement morning AM dosage for pets, particularly feline pets, consisting essentially of:

| Anti-Oxidant Vitamins | |
|---|---|
| Vitamin A (Palmitate, Alpha Carotene, Lycopene and other Carotenoids) | 113 IU |
| Vitamin C (Ascorbic Acid) | 17 mg |
| Vitamin E (d-Alpha Tocopheryl acetate) | 5.0 IU |
| Lutein | 1.0 mcg |
| Coenzyme Q10 | 1.0 mg |
| B Complex Vitamins | |
| Vitamin B-1 (Thiamine Hydrochloride) | 1.3 mg |
| Vitamin B-2 (Riboflavin Powder) | 0.55 mg |
| Vitamin B-3 (Niacin) | 1.0 mg |
| Vitamin B-3 (Niacinamide) | 12.5 mg |
| Vitamin Biotin | 8.3 mcg |
| Vitamin Folic Acid | 8.3 mcg |
| Vitamin B-12 (Cyanocobalamin) | 8.3 mcg |
| Vitamin B-5 (Calcium Pantothenate) | 2.5 mg |
| Vitamin B-6 (Pyridoxine HCL) | 0.415 mg |
| Inositol | 31.3 mg |
| Bioflavonoids | |
| Lemon Bioflavonoids | 3.125 mg |
| Chelated Minerals | |
| Zinc Gluconate | 1.0 mg |
| Selenium Chelate | 4.4 mcg |
| Chromium Chelate | 12.5 mcg |
| Vanadyl Sulfate | 8.3 mcg |
| Calcium Citrate | 1.0 mg |
| Magnesium Oxide | 1.875 mg |
| Manganese Malate | 0.65 mg |
| Digestive Enzymes | |
| Digestive Enzyme Complex (full range) consisting of: | 1.25 mg |
| Protease | 7.5 Units |
| Amylase | 30 Units |
| Lipase | 1.25 Units |
| Cellulase | 0.25 Units |
| Lactase | 5.0 Units |
| Herbs | |
| Green Tea Extract (30% polyphenols) | 17.5 mg |
| Siberian Ginseng (root) | 12.5 mg |
| Nutrients | |
| Glucosamine Hydrochloride | 100 mg |
| MSM | 31.25 mg |
| Alpha Lipoic Acid | 1.0 mg |
| L-Lysine | 12.5 mg |
| L-Taurine | 12.5 mg |
| L-Carnitine | 1.25 mg |

-continued

Essential Fatty Acids

| | |
|---|---|
| Gamma Linolenic Acid (Borage Seed Oil) | 5.0 mg. |

2. A health and nutritional supplement dosage for pets according to claim 1, wherein the dosage is in capsule form.

3. A health and nutrition supplement evening PM dosage for pets, particularly feline pets, consisting essentially of:

Anti-Oxidant Vitamins

| | |
|---|---|
| Vitamin A (Palmitate, Alpha Carotene, Lycopene and other Carotenoids) | 113 IU |
| Vitamin C (Ascorbic Acid) | 17 mg |
| Vitamin E (D-Alpha Tocopherols acetate) | 5.0 IU |

B Complex Vitamins

| | |
|---|---|
| Vitamin B-1 (Thiamine Hydrochloride) | 1.3 mg |
| Vitamin B-2 (Riboflavin Powder) | 0.55 mg |
| Vitamin B-3 (Niacin) | 1.0 mg |
| Vitamin B-3 (Niacinamide) | 5.0 mg |
| Vitamin Biotin | 8.3 mcg |
| Vitamin Folic Acid | 8.3 mcg |
| Vitamin B-12 (Cyanocobalamin) | 8.3 mcg |
| Vitamin B-5 (Calcium Pantothenate) | 2.5 mg |
| Vitamin B-6 (Pyridoxine Hydrochloride) | 0.415 mg |
| Choline Bitartrate | 1.25 mg |
| Inositol | 31.3 mg |

-continued

Bioflavonoids

| | |
|---|---|
| Lemon Bioflavonoids | 3.125 mg |

Chelated Minerals

| | |
|---|---|
| Zinc Gluconate | 1.0 mg |
| Selenium Chelate | 4.4 mcg |
| Chromium Chelate | 12.5 mcg |
| Vanadyl Sulfate | 8.3 mcg |
| Calcium (Citrate) | 1.0 mg |
| Magnesium Oxide | 1.875 mg |
| Manganese Malate | 0.65 mg |

Digestive Enzymes

| | |
|---|---|
| Digestive Enzyme Complex | 1.25 mg |

Nutrients

| | |
|---|---|
| Colostrum | 0.65 mg |
| Whey Peptides (Hydrolyzed Whey Protein) | 7.0 mg |
| Melatonin | 0.095 mg |

Amino Acids

| | |
|---|---|
| L-Glutamine | 31.25 mg |
| L-Carnitine | 0.65 mg |
| L-Lysine | 12.5 mg |
| L-Taurine | 12.5 mg. |

4. A health and nutritional supplement dosage for feline pets according to claim 3 wherein the dosage is in a capsule form.

* * * * *